United States Patent [19]

Batty et al.

[11] 4,344,994

[45] Aug. 17, 1982

[54] SIGN LETTERING MATERIALS

[75] Inventors: Mark J. Batty, London, England; Thomas Groth, Ljan, Norway

[73] Assignee: Letraset USA, Inc., Paramus, N.J.

[21] Appl. No.: 16,601

[22] Filed: Feb. 21, 1979 (Under 37 CFR 1.47)

[30] Foreign Application Priority Data

Feb. 17, 1978 [GB] United Kingdom ................ 6434/78

[51] Int. Cl.[3] ......................... A61F 13/02; G09F 7/16

[52] U.S. Cl. ........................................ 428/41; 40/595; 428/40; 428/207; 428/914

[58] Field of Search ..................... 428/40, 41, 42, 187, 428/195, 207, 914; 40/595

[56] References Cited

U.S. PATENT DOCUMENTS

| | | | |
|---|---|---|---|
| 3,130,984 | 4/1964 | Fenberg | 428/195 |
| 3,440,746 | 4/1969 | Richards | 40/595 |
| 3,945,141 | 3/1976 | Frost | 428/195 |
| 4,015,352 | 4/1977 | Prange | 428/41 |
| 4,089,722 | 5/1978 | Holubek | 428/187 |
| 4,125,658 | 11/1978 | Miles | 428/195 |

FOREIGN PATENT DOCUMENTS

| | | |
|---|---|---|
| 1109792 | 4/1968 | United Kingdom . |
| 1115922 | 6/1968 | United Kingdom . |
| 1465473 | 2/1977 | United Kingdom . |
| 1474742 | 5/1977 | United Kingdom . |
| 1493103 | 11/1977 | United Kingdom . |
| 1095588 | 12/1977 | United Kingdom . |

*Primary Examiner*—William R. Dixon, Jr.
*Attorney, Agent, or Firm*—Darby & Darby

[57] ABSTRACT

Sign lettering materials are described which consist of plastics film letters releasably adhered to a split backing tile, e.g. of silicone coated card, by a permanently tacky pressure-sensitive adhesive. In order to assist proper spacing of these letters (and numbers) when they are set up to form words, in the case of at least some of the letters of the alphabetic set, one or more corners of the tile has a stepped notch with one or more steps. The inmost vertical sides of the notches are abutted to give the desired spacing, consistent with the letters not overlapping. The system allows visually even spacing to be rapidly achieved over a range from closely spaced letters to wide spacing.

8 Claims, 8 Drawing Figures

SIGN LETTERING MATERIALS

This invention relates to sign lettering materials. For simplicity of expression the term "lettering" is used herein to include both letters, figures and typographical symbols such as &, £ and @.

Sign lettering materials have been known for some years and are described for example in British Patent Specifications Nos. 1109792 and 1115922.

The classical way of arranging to space such sign lettering materials has been to butt the edges of the temporary carrier tiles on which the letters were mounted but this system does not work well if it is desired to space the letters fairly closely. In recent years various suggestions have been of modifications to the basic sign lettering which would enable the backing tile to be used to achieve close spacing. British Patent Specifications Nos. 1465473, 1474742 and 1493103 describe systems of this type. All of these systems suffer from the disadvantage that they are relatively inflexible, i.e. each allows for one and only one spacing between a pair of adjacent letters. It is desirable to give the user of such sign lettering materials greater freedom of choice than this.

Figure 1A:
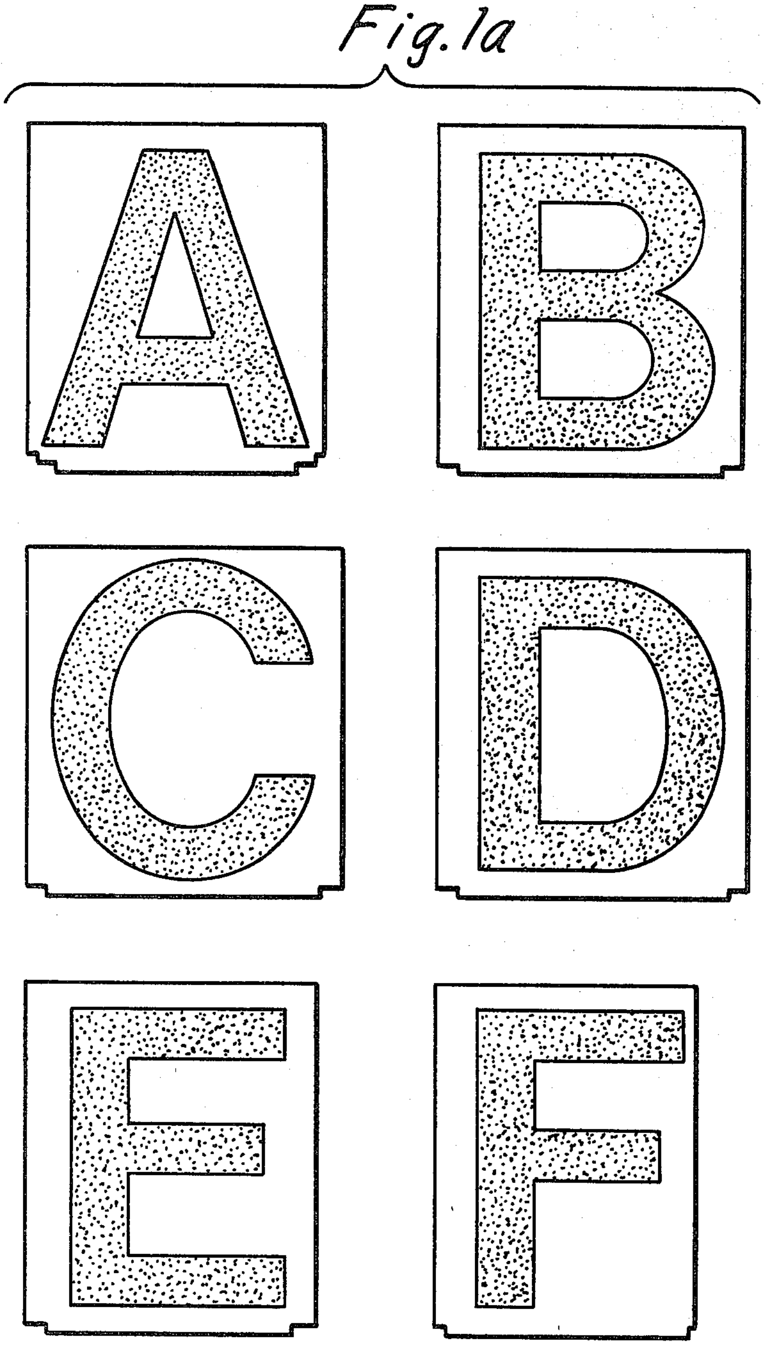
Figure 1A:
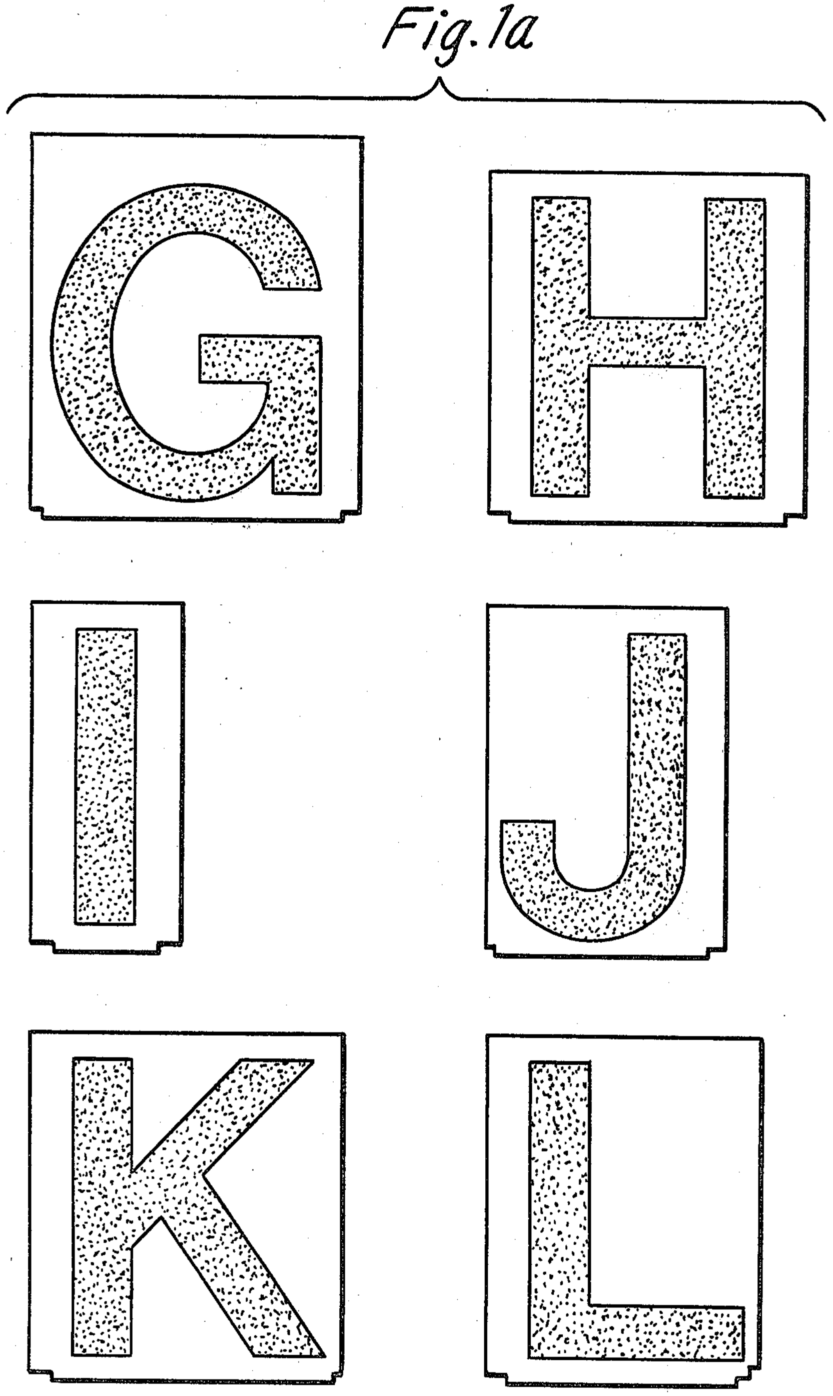
Figure 1A:
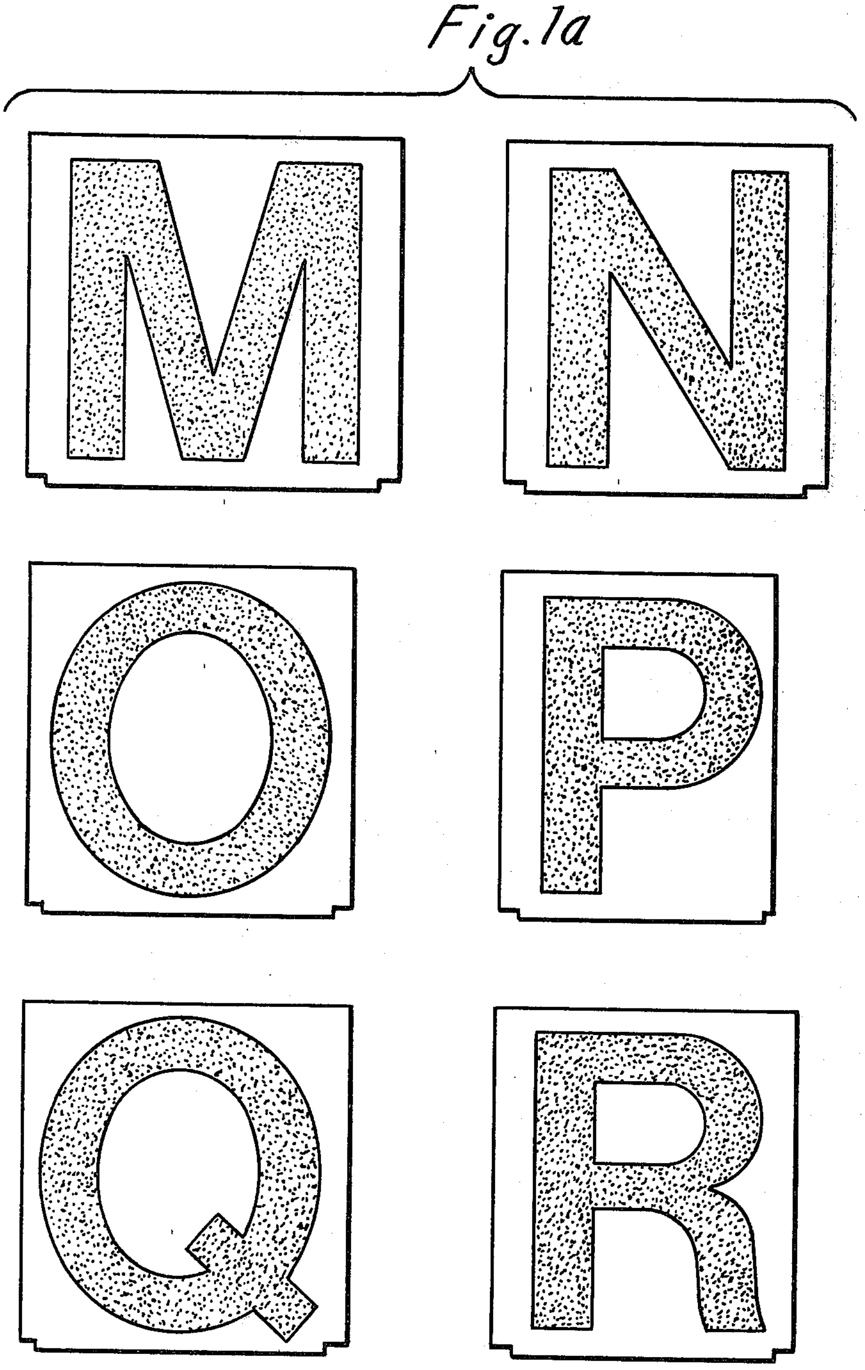
Figure 1A:
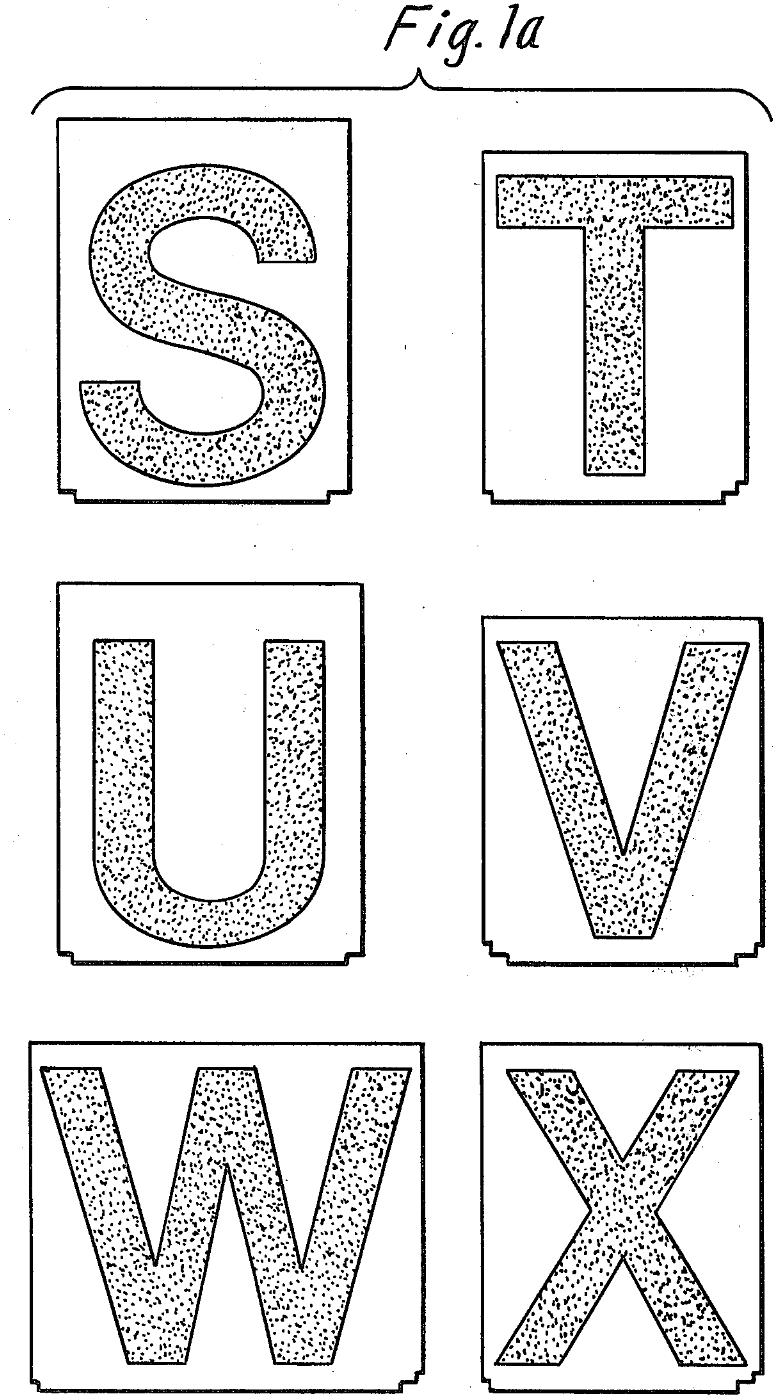
Figure 1A:
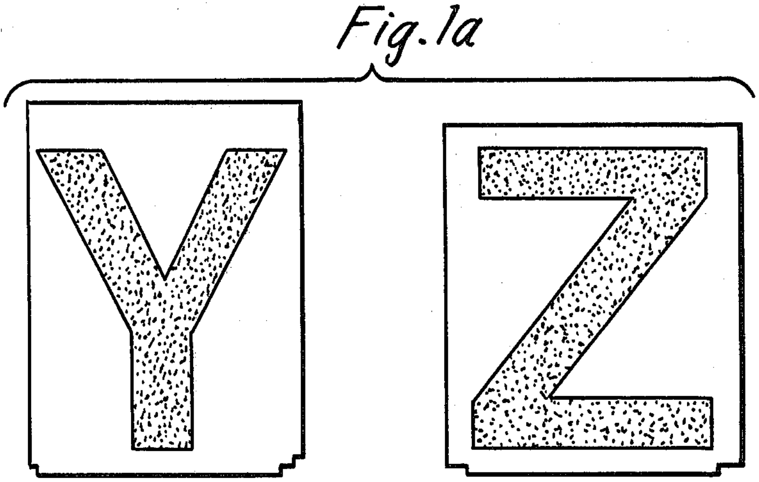
Figure 1C:
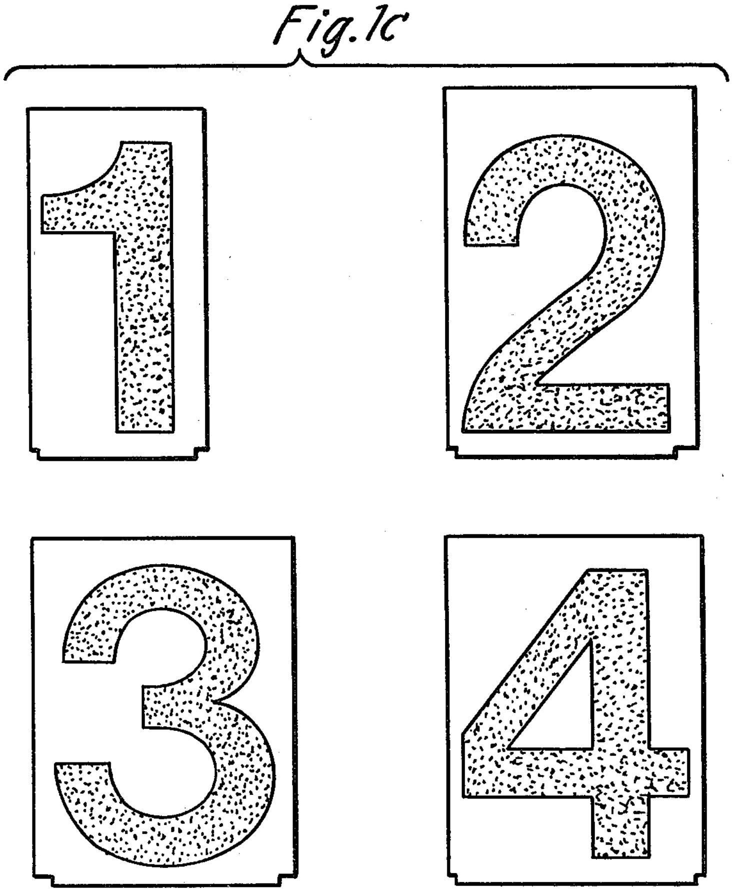
Figure 1B:
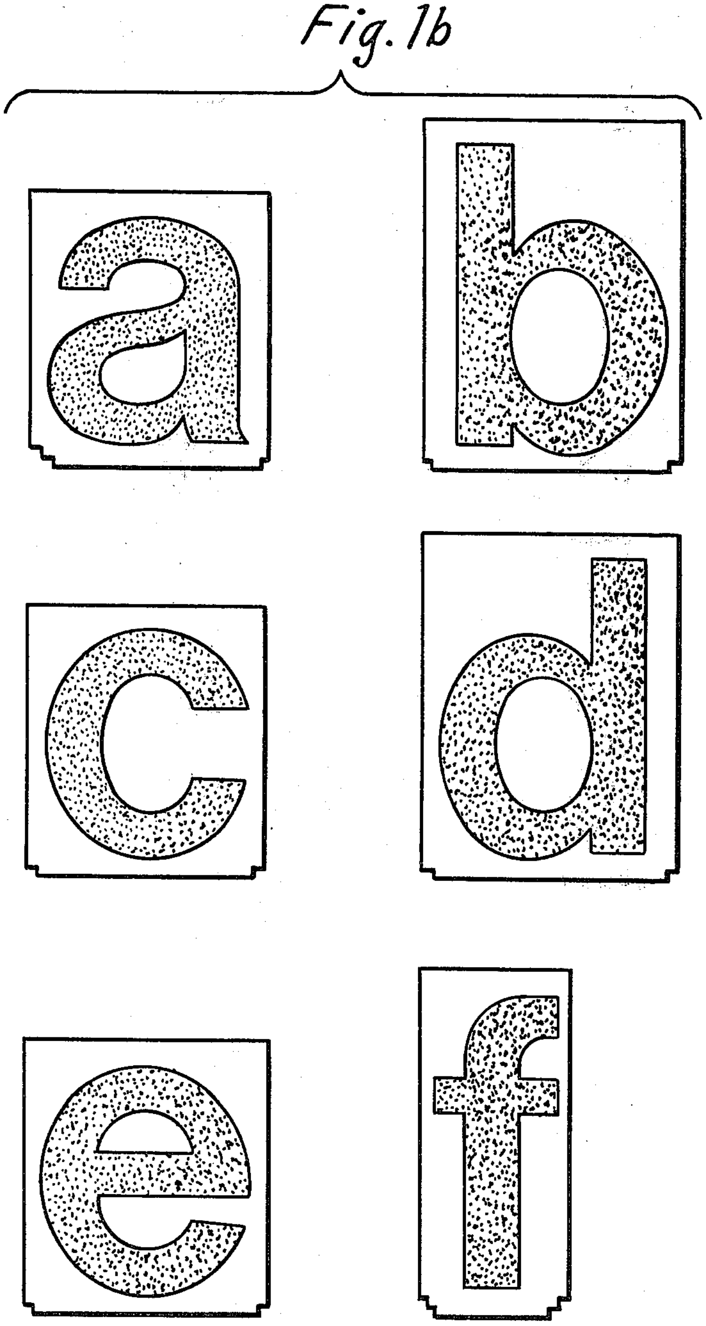
Figure 1B:
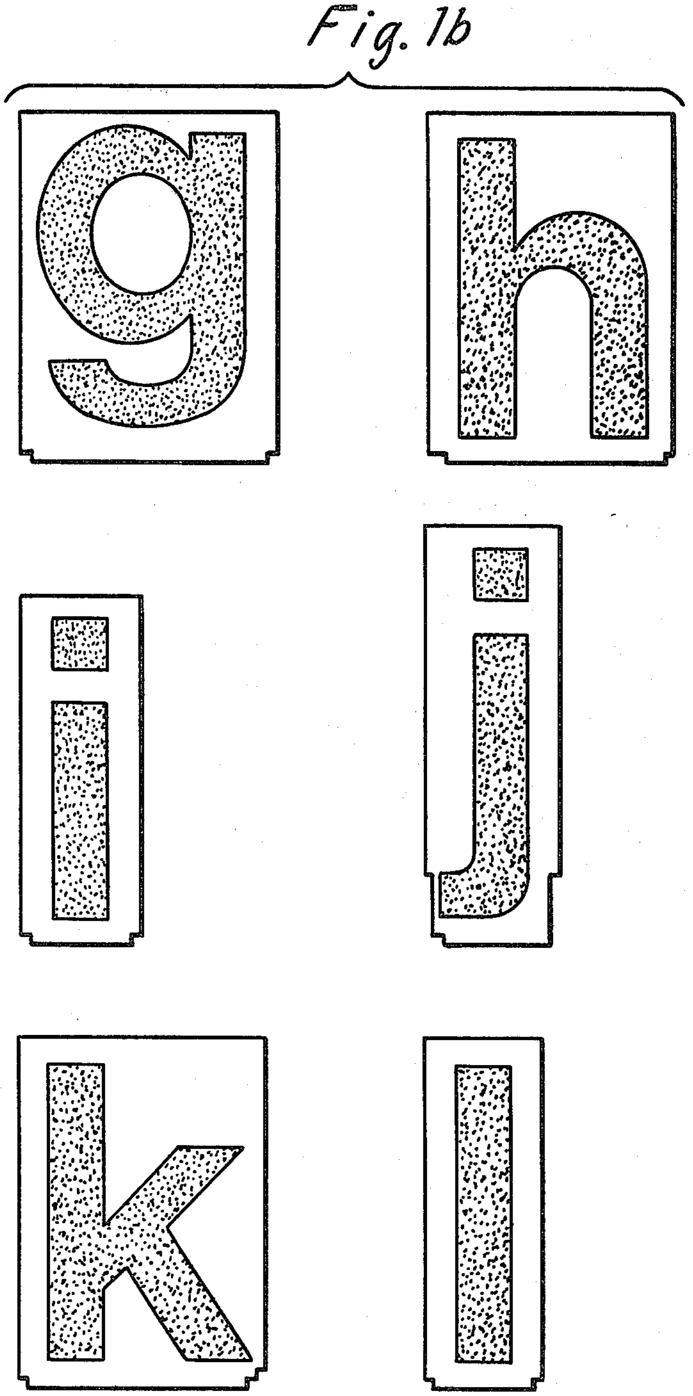
Figure 1B:
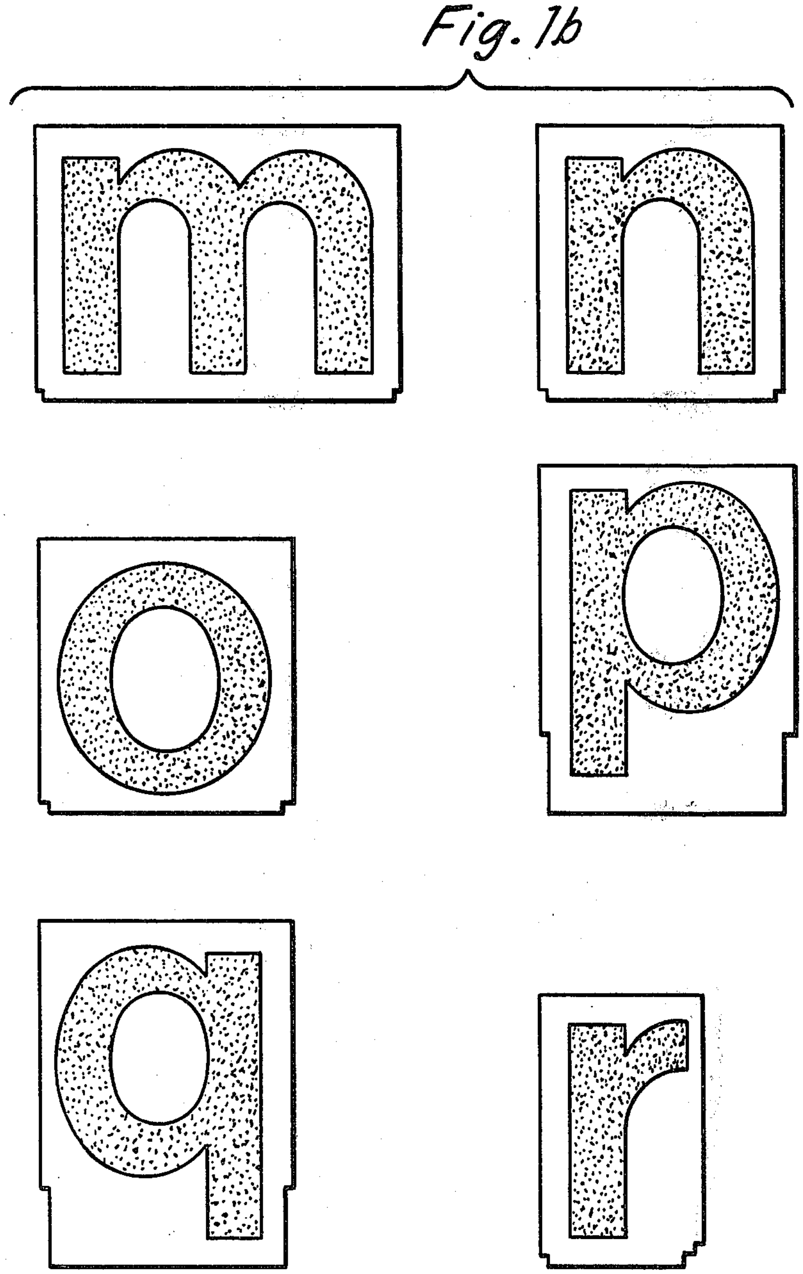
Figure 1B:
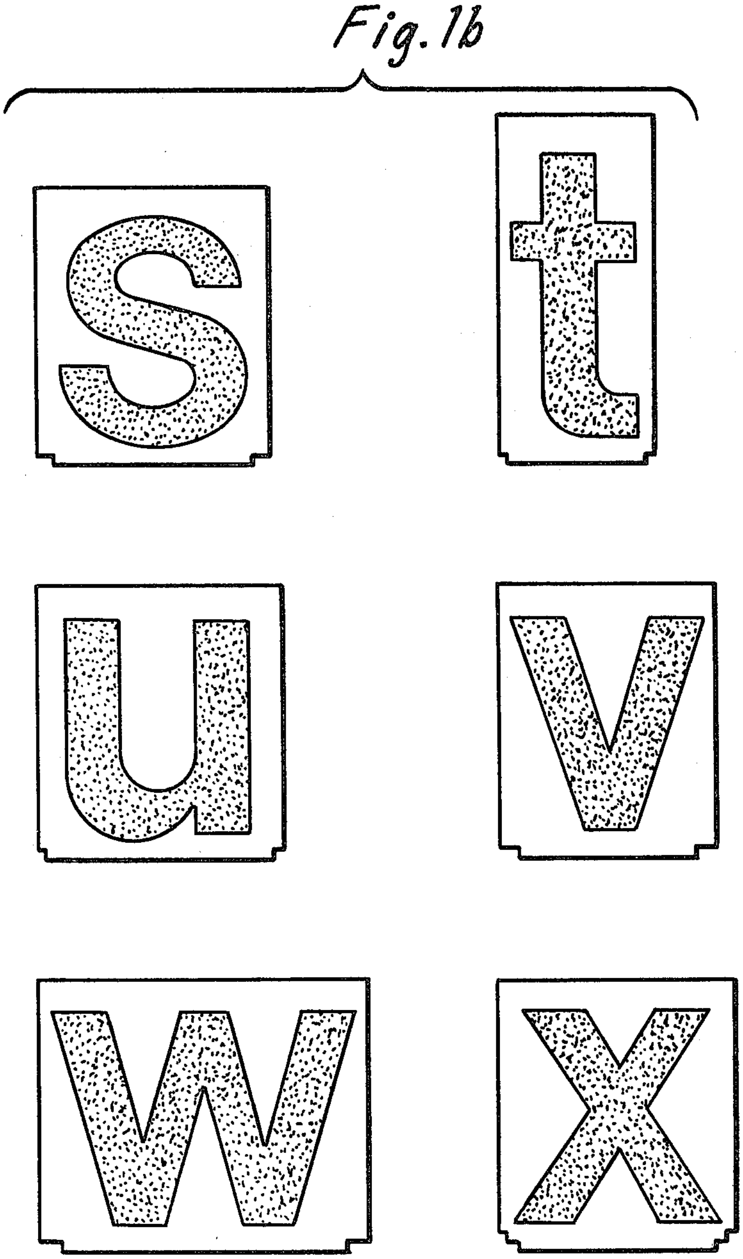
Figure 1B:
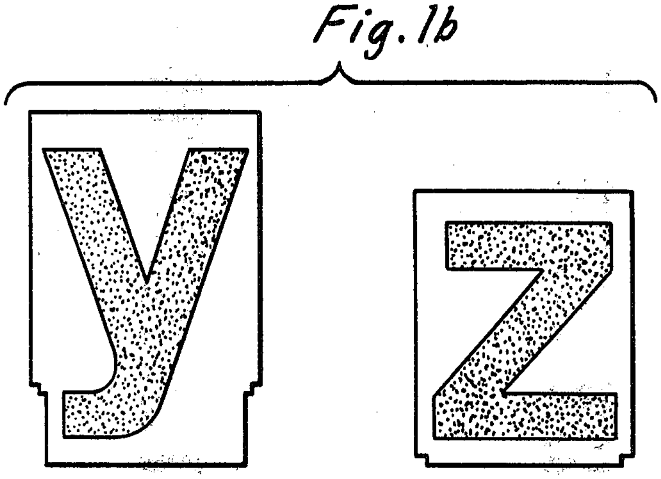
Figure 1C:
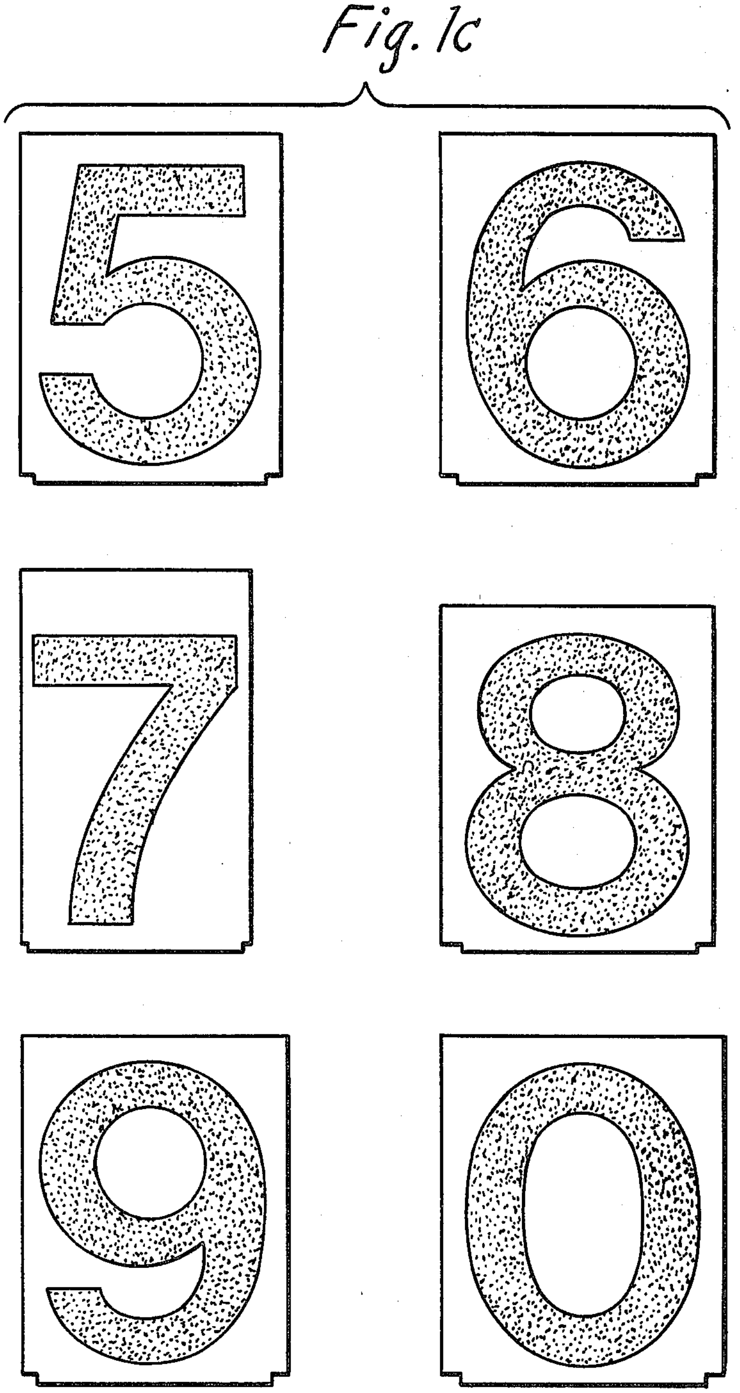
Figure 2A:
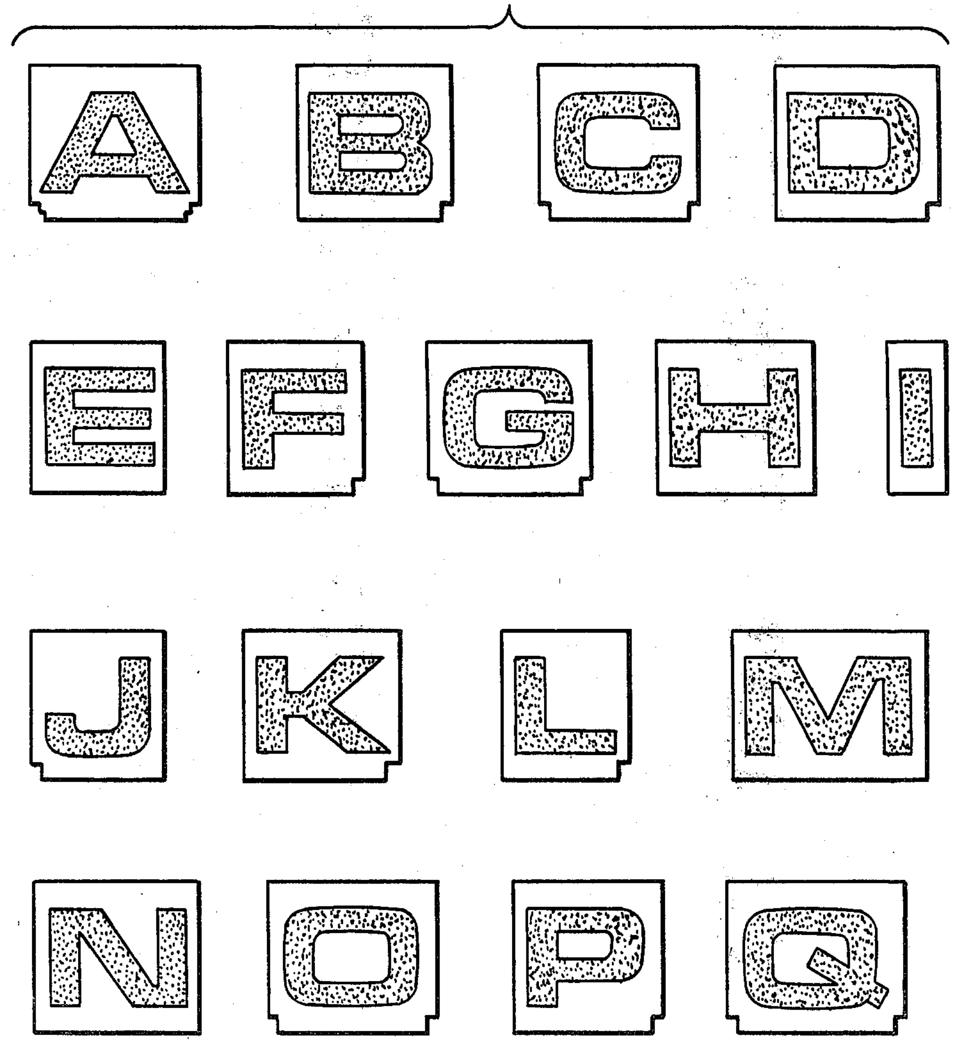
Figure 2A:
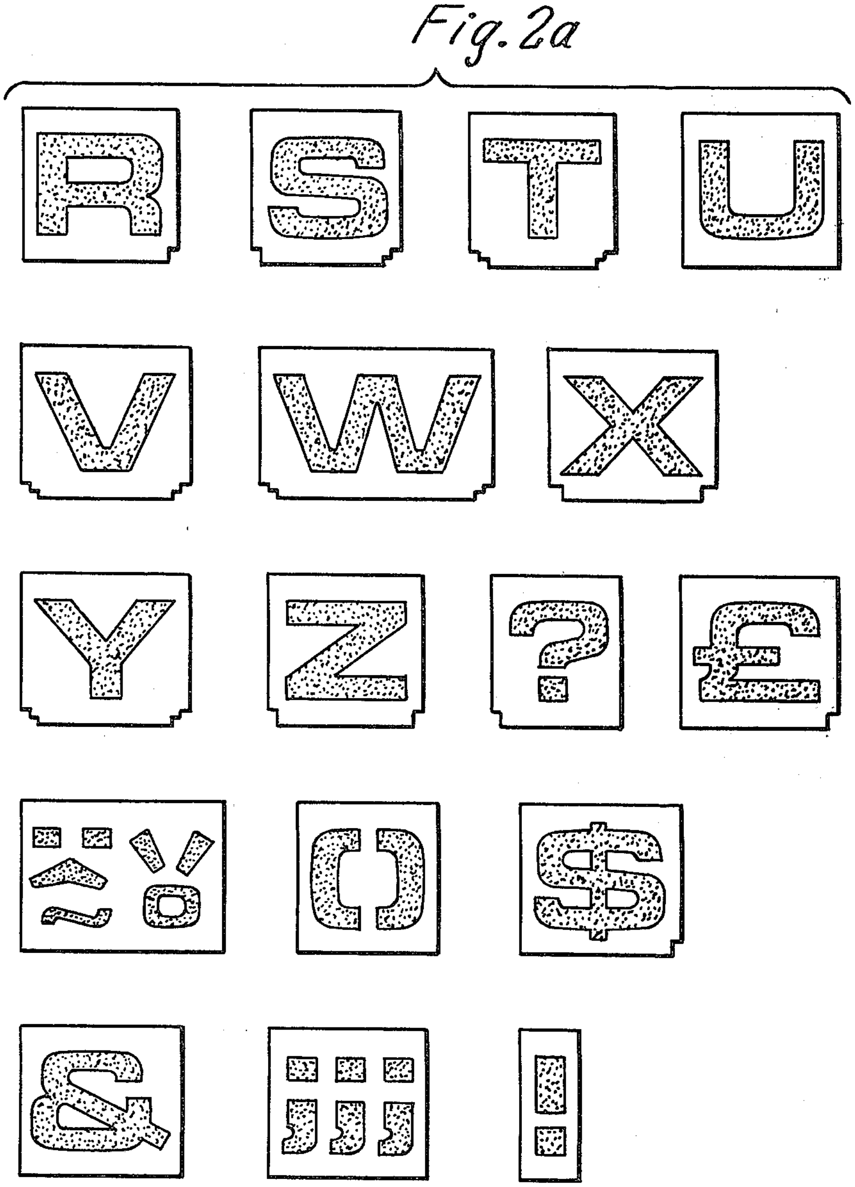
Figure 2B:
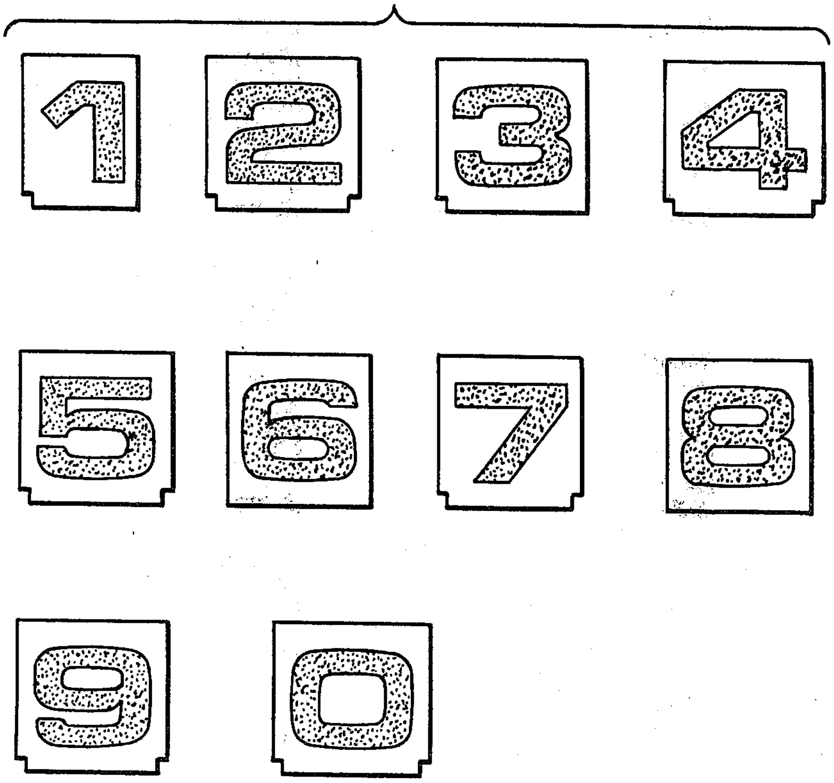
Figure 3:
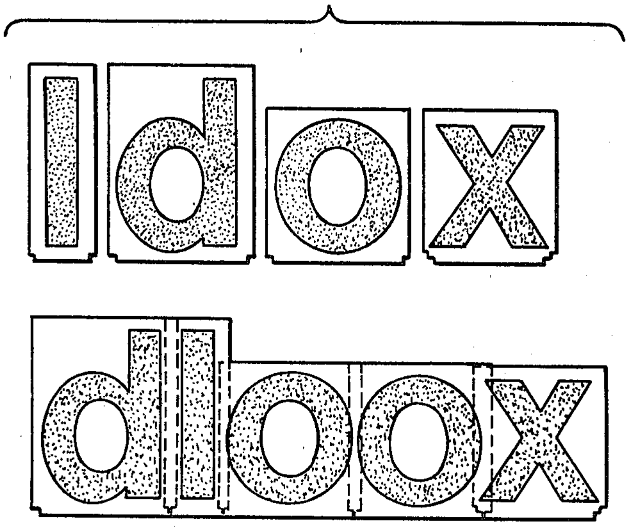
Figure 4:
Figure 5:
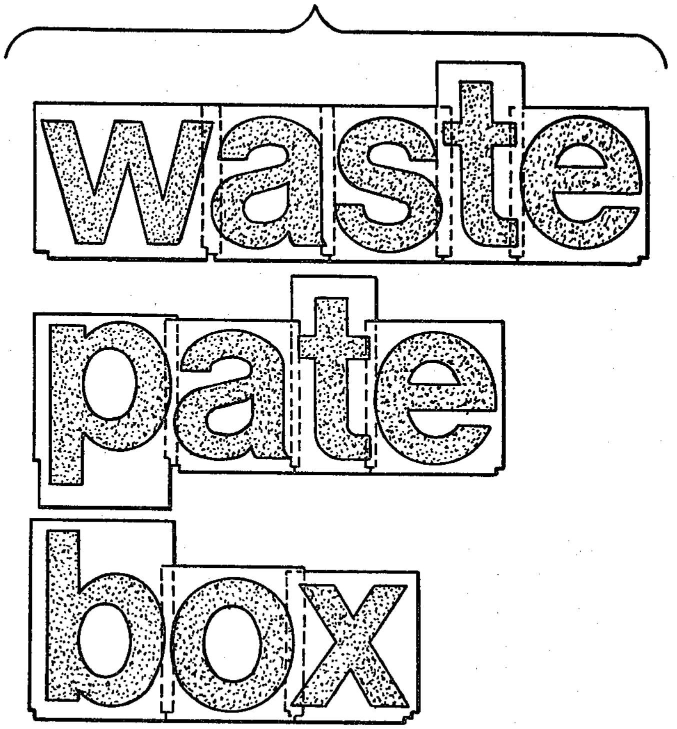

The invention is illustrated by way of Example with reference to the accompanying drawings in which:

FIGS. 1*a*, 1*b* and 1*c* show a set of tiles bearing a complete alphabet in upper case (FIG. 1*a*), lower case (FIG. 1*b*) and numbers (FIG. 1*c*);

FIG. 2*a* shows a further complete upper case alphabet plus accidentals, and FIG. 2*b* the matching numerals, FIG. 3 shows a set of four letters in unspaced and properly spaced arrangements, FIG. 4 shows three properly spaced words using upper case letters, and FIG. 5 shows the same three words, properly spaced, using lower case letters.

According to the present invention there is provided a sign lettering material comprising a set of letters each individually mounted on a split backing tile wherein, in the case of at least some of the letters, one portion of the tile has at each corner a stepped notch having one or more steps.

Such a lettering material is used in the following way: when two letters each having an associated notched tile are to be placed adjacent to one another, with close spacing between the letters, the first letter is laid down in the usual way with the part of its tile bearing the notches remaining adhered to the letter. The second letter is the brought into position so that the vertical edge of the innermost step of the notch on the tile of the second letter coincides with the vertical edge of the step of the notch innermost from the edge of the tile on the first letter. If in this position the letters themselves overlap, then the two tiles are moved apart by one or more steps of the notches sufficiently to remove the overlap. Successive letters are laid down in this way to form a legend in which the letters are properly close spaced. If instead of that close spacing a more open spacing is required then in each case the letters are moved apart to leave an identical size gap between each pair of previously butted vertical edges. The wider spacing so achieved still has an optically even appearance, since it is based on the original proper close spacing between the letters. In this way, any combination of characters can be properly set up correctly spaced to look even.

It is found that in any particular alphabet, not all of the tiles need to carry a notch and that the notches in some tiles may require only one step while those in others may require two or even three steps.

The notches are conveniently and preferably formed as rectangular stepped notches on the lower corners of the lower part of the backing as viewed. The two stepped notches may be mirror images of one another in the case of some letters, or may be of different proportions or numbers of steps in the case of others.

The conventional way of making sign lettering materials of the type according to the invention is by die-cutting from a web of plastics foil/release card laminate. The notches may conveniently be formed at the same time as the letter is cut out, ensuring perfect relative positioning between the letter and the notches. The die for cutting the notches may also cut out the tile and form the split in the backing, though splitting the backing is conveniently effected prior to die-cutting by a standard slitter.

The split backing tile may be made of release coated card stock, or of any other appropriate material. The backing tile may be opaque, translucent or transparent.

We claim:

1. A sign lettering material comprising a set of die cut letters each of said letters being individually adhesively mounted on a backing tile, the tile being substantially rectangular and formed in two portions separated by a split running substantially horizontally across the letter and enabling removal of one portion of the tile to leave part of the letter with its adhesive surface exposed and the remainder of the letter adherent to the other portion of the tile, wherein, in the case of at least some of the letters, one portion of the tile has in each corner, constituting a corner of the substantially rectangular tile a stepped notch having one or more steps, and at least some of the letters in the set having at least two steps on the notches of their respective tiles.

2. A sign lettering material according to claim 1 wherein in the set some tiles carry no notches, some carry one-stepped notches and others carry two-stepped notches.

3. A sign lettering material according to claim 1 wherein the notches are located on the lower corners of the lower part of the split backing as seen when the letter is viewed right way up.

4. A sign lettering material according to claim 1 wherein the notches are die-cut in the backing tile simultaneously with die-cutting the letter.

5. A sign lettering material according to claim 1 wherein said letters comprise a plastic film.

6. A sign lettering material according to claim 5 wherein said plastic film letters are releasably adhered to said split backing tile.

7. A sign lettering material consisting essentially of a set of die-cut alphabet letters, each of said letters being individually mounted on a split backing tile, one portion of the split backing tile on at least some of the letters in said letter set having a notch in one corner thereof, said notch having at least one right-angle step.

8. A sign lettering material comprising a set of die cut letters including at least one of each letter of the alphabet, each of said letters being adhesively mounted on an individual split backing tile, the split backing tile on the letters C, D, E, F, G, H, I, J, K, M, N, O, P, Q, R, S, U, and Z having a notch with a single right-angle step in two opposite corners thereof, the split backing tile on the letters A and V having notches including two right angles steps in two opposing corners thereof, and the letters L, T, W, X and Y being formed on a split backing tile bearing in one corner thereof a notch including one right angle step and in an opposite corner thereof a notch including two right angle steps.

* * * * *